US00PP19946P3

(12) United States Plant Patent
Korlipara

(10) Patent No.: US PP19,946 P3
(45) Date of Patent: Apr. 21, 2009

(54) *COREOPSIS* PLANT NAMED 'GOLD NUGGET'

(50) Latin Name: *Coreopsis*
Varietal Denomination: Gold Nugget

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/901,047

(22) Filed: Sep. 13, 2007

(65) Prior Publication Data

US 2009/0077700 P1 Mar. 19, 2009

(51) Int. Cl.
*A01H 5/00* (2006.01)

(52) U.S. Cl. ..... Plt./417

(58) Field of Classification Search ..... Plt./417
See application file for complete search history.

(56) References Cited

PUBLICATIONS

U.S. Appl. No. 11/474,021, filed Jun. 23, 2006, Korlipara.

*Primary Examiner*—Annette H Para
*Assistant Examiner*—June Hwu
(74) *Attorney, Agent, or Firm*—Klarquist Sparkman, LLP

(57) ABSTRACT

A new and distinct *Coreopsis* plant named 'Gold Nugget' characterized by prolific, large, bright yellow and maroon daisy-type flowers, grass green foliage, very free branching and flowering, long bloom time, and a mounding habit.

1 Drawing Sheet

Figure 1:
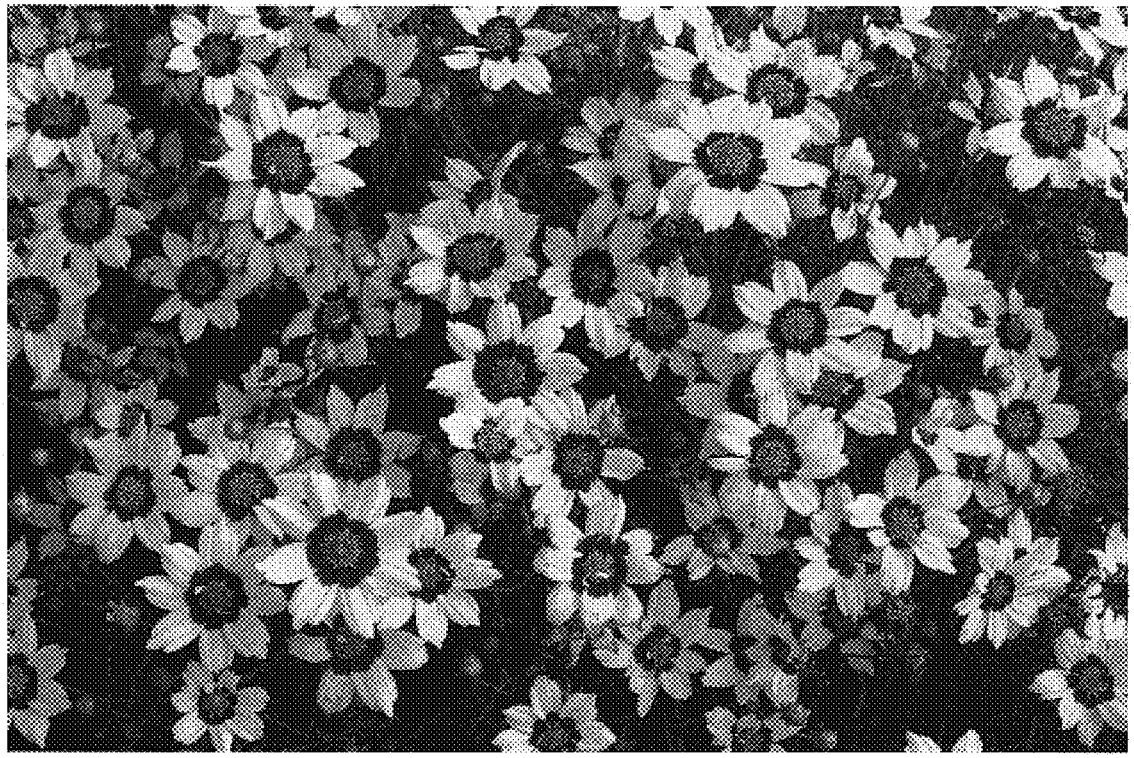

Botanical denomination: *Coreopsis* hybrid.
Variety designation: 'Gold Nugget'.

BACKGROUND OF THE INVENTION

The present invention relates to a new and distinct hybrid of *Coreopsis* and given the cultivar name 'Gold Nugget'. *Coreopsis* is in the family *Asteraceae.* This new cultivar originated from a branch sport from *Coreopsis* 'Snowberry' (U.S. Plant Pat. No. 18/560) grown in a controlled greenhouse environment.

SUMMARY OF THE INVENTION

The following traits have been repeatedly observed and are determined to be the unique characteristics of the new variety. These characteristics in combination distinguish *Coreopsis* 'Gold Nugget' as a new and distinct cultivar:

1. Large, daisy-type flowers that grow to 4.5 cm in diameter;
2. Unique, bright yellow and maroon bi-colored ray florets;
3. Grass green foliage;
4. Very free branching;
5. Very free flowering;
6. Long bloom time;
7. Mounding habit.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a nine-month-old *Coreopsis* 'Gold Nugget' growing in the ground in the trial field in August 2007, in Canby, Oreg.

DETAILED PLANT DESCRIPTION

The following is a detailed description of the new *Coreopsis* cultivar based on observations of a nine-month-old specimen growing in the ground in full sun under typical outdoor conditions in the trial fields in August 2007, in Canby, Oreg. Canby is Zone 8 on the USDA Hardiness map. Temperatures range from a high of 95 degrees F. in August to a low of 32 degrees F. in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zones 7 to 10.
- *Size.*—55 cm wide and 40 cm tall to top of inflorescences.
- *Form.*—Mound.
- *Vigor.*—Excellent.
- *Roots.*—Fibrous, Grey Brown 199D, stems root easily from stem cuttings.

Stem:
- *Type.*—Ascending.
- *Size.*—32 cm tall and 4 mm wide.
- *Internode length.*—5 to 30 mm.
- *Surface.*—Glabrous.
- *Color.*—Green 137A.

Leaf:

*Type.*—Simple.

*Shape.*—Linear.

*Arrangement.*—Opposite.

*Length including petiole.*—Grows to 6.5 cm.

*Width.*—3 mm.

*Margins.*—Entire.

*Apex.*—Acuminate.

*Base.*—Attenuate, clasping.

*Surface texture.*—Glabrous on both sides.

*Venation.*—Pinnate.

*Color.*—Top side Yellow Green 147A, bottom side Yellow Green 147B.

Inflorescence:

*Type.*—Long stalked terminal heads of daisy type inflorescences.

*Peduncle.*—6 to 9 cm tall, 1 mm wide, glabrous, Yellow Green 147B.

*Size.*—Grows to 5 cm wide and 18 mm deep.

*Immature.*—8 mm long and 5 mm wide, ovoid, glabrous, Greyed Yellow 161A on top half with Yellow Green 146A on bottom half.

*Receptacle.*—Bowl shaped, 5 mm wide and 5 mm deep, Green 137A.

*Phyllary.*—In two series, stellate; inner series 8 lobes, grows to 16 mm wide and 7 mm deep, lobes reflex, ovate, entire, acute, glabrous, 7 mm long and 5 mm wide, on both sides top half Yellow Orange 22A tipped with Greyed Purple 187A, bottom half Yellow Green 147A; outer series with 6 to 8 lobes, grows to 10 mm wide and 3 mm deep, glabrous, lobes lanceolate, entire, acute, 3.5 mm long and 1.5 mm wide, Green 137A on both sides.

*Bloom period.*—June through September in Canby, Oreg.

*Fragrance.*—Light, Chrysanthemum-like.

*Lastingness.*—Each inflorescence lasts about 7 to 10 days.

Florets:

*Type.*—Composite.

*Ray florets.*—8 with no stamen or pistil, obovate with the tip usually three lobed with lobes obtuse and notched and the central lobe the longest, entire, grows to 25 mm long, 12 mm wide, glabrous on both surfaces, claw 3 mm long, topside Yellow 12A with Greyed Purple 187B at base, bottom side Yellow 4D with Greyed Green 197A at base.

*Disc.*—Conic, deeper with maturity, 7 mm wide and becoming 3 mm deep with maturity, Greyed Orange 163C when in bud, opening to Greyed Orange 163A.

*Disc florets.*—About 70 in number, 10 mm long and 1 mm wide, corolla 5 mm long, tubular, 4 lobed, lobes entire, acute, Orange 24B, tube Yellow 2B; pistil 1, 12 cm long, ovary 2 mm long, Green White 157A, style 7 mm long, extruding, with 2-branched stigma, stigma Orange 24B and style Yellow 4C; stamen 5, 3.5 mm long, filaments 1 mm long, Yellow 2B, anthers 2.5 mm long, Black 202A, pollen Yellow 12A.

Seed: none produced.

*Fertility.*—Infertile.

Disease and pests: *Coreopsis* are susceptible to mildew and fungal spots. No resistance is known for this variety.

COMPARISONS TO SIMILAR *COREOPSIS*

Compared to *Coreopsis* 'Snowberry' (U.S. Plant Pat. No. 18,560), the mother plant, the new variety has bright yellow rather than creamy white ray florets. Both flowers have a distinctive maroon eye.

Compared to *Coreopsis* 'Autumn Blush' (U.S. Plant Pat. No. 18,184), the new variety has a much darker yellow ray floret color.

I claim:

1. A new and distinct *Coreopsis* plant as herein illustrated and described.

* * * * *